United States Patent
Sharma et al.

(10) Patent No.: US 7,415,307 B2
(45) Date of Patent: Aug. 19, 2008

(54) ISCHEMIA DETECTION BASED ON CARDIAC CONDUCTION TIME

(75) Inventors: Vinod Sharma, Roseville, MN (US); Walter H. Olson, North Oaks, MI (US)

(73) Assignee: Medtronic, Inc., Minneapolis, MN (US)

( * ) Notice: Subject to any disclaimer, the term of this patent is extended or adjusted under 35 U.S.C. 154(b) by 589 days.

(21) Appl. No.: 10/284,900

(22) Filed: Oct. 31, 2002

(65) Prior Publication Data

US 2004/0088017 A1    May 6, 2004

(51) Int. Cl.
*A61N 1/00* (2006.01)
(52) U.S. Cl. ................................. 607/17; 600/509
(58) Field of Classification Search ............. 600/516, 600/509, 508; 607/17, 25
See application file for complete search history.

(56) References Cited

U.S. PATENT DOCUMENTS

| | | | | |
|---|---|---|---|---|
| 4,681,117 A | * | 7/1987 | Brodman et al. | 600/374 |
| 5,135,004 A | | 8/1992 | Adams et al. | 128/696 |
| 5,243,976 A | | 9/1993 | Ferek-Petric et al. | 607/6 |
| 5,243,981 A | * | 9/1993 | Hudrlik | 607/11 |
| 6,021,350 A | | 2/2000 | Mathson | 607/17 |
| 6,122,545 A | * | 9/2000 | Struble et al. | 607/9 |
| 6,128,526 A | | 10/2000 | Stadler et al. | 600/517 |
| 6,243,603 B1 | * | 6/2001 | Ideker et al. | 607/5 |
| 6,361,503 B1 | * | 3/2002 | Starobin et al. | 600/508 |
| 6,424,865 B1 | * | 7/2002 | Ding | 607/9 |
| 6,514,195 B1 | * | 2/2003 | Ferek-Petric | 600/17 |
| 6,609,023 B1 | * | 8/2003 | Fischell et al. | 600/515 |
| 6,648,829 B2 | * | 11/2003 | Starobin et al. | 600/508 |
| 6,652,467 B2 | * | 11/2003 | Starobin et al. | 600/508 |
| 6,763,267 B2 | * | 7/2004 | Ding | 607/9 |
| 6,768,919 B2 | * | 7/2004 | Starobin et al. | 600/520 |
| 6,931,281 B2 | * | 8/2005 | Bradley et al. | 607/9 |
| 7,066,891 B2 | * | 6/2006 | Stadler et al. | 600/508 |
| 2002/0016548 A1 | | 2/2002 | Stadler et al. | 600/509 |

(Continued)

FOREIGN PATENT DOCUMENTS

WO    WO 97/24981    7/1997

(Continued)

OTHER PUBLICATIONS

Badir, B. et al., "Continuous ST-Segment Monitoring During Coronary Angioplasty Using Orthogonal ECG Leads," *Journal of Electrocardiology*, vol. 30, No. 3, p. 175-87 (1997).

(Continued)

*Primary Examiner*—Carl H. Layno
*Assistant Examiner*—Brian T Gedeon
(74) *Attorney, Agent, or Firm*—Paul H. McDowall; Michael C. Soldner; Steve Bauer

(57) ABSTRACT

Methods and process for detection of myocardial ischemia involve detection and analysis of changes in electrical conduction velocity within the heart to monitor changes in the condition of the cardiac muscle and indicate possible ischemia. Conduction velocity slows considerably when oxygen supply to the heart is reduced. Analysis of electrical conduction velocity can be used to verify the occurrence of myocardial ischemia in a more reliable manner. Changes in conduction velocity may be monitored based on conduction time between electrodes positioned in the left and right ventricles of the heart. The electrodes may be endocardial or epicardial electrodes. In general, the techniques may involve launching a stimulation waveform at one electrode and sensing a local cardiac depolarization at another electrode to assess conduction time.

33 Claims, 11 Drawing Sheets

U.S. PATENT DOCUMENTS

| | | | |
|---|---|---|---|
| 2002/0042578 A1* | 4/2002 | Starobin et al. | 600/508 |
| 2002/0072777 A1 | 6/2002 | Lu | 607/17 |
| 2002/0165459 A1* | 11/2002 | Starobin et al. | 600/509 |
| 2002/0193694 A1* | 12/2002 | Anosov et al. | 600/509 |
| 2003/0023184 A1 | 1/2003 | Pitts-Crick et al. | 600/547 |
| 2004/0122478 A1* | 6/2004 | Stadler et al. | 607/17 |
| 2005/0038351 A1* | 2/2005 | Starobin et al. | 600/516 |

OTHER PUBLICATIONS

Cascio, W. et al., "Electrical Properties and Conduction in Reperfused Papillary Muscle," *Circuit Research*, vol. 89, p. 807-14 (2001).

Geller, J. et al., "Persistent T-Wave Changes After Alteration of the Ventricular Activation Sequence: New Insights Into Cellular Mechanisms of 'Cardiac Memory,'" *Circulation*, vol. 88, No. 4, Pt 1, p. 1811-9 (Oct. 1993).

Kurita, T. et al., "The Electrophysiologic Mechanism of ST-Segment Elevation in Brugada Syndrome," *J Amer Coll Cardiol*, vol. 40, No. 2, p. 330-4 (Jul. 17, 2002).

Stadler, R. et al., "A Real-time ST-Segment Monitoring Algorithm for Implantable Devices," *Journal of Electrocardiology*, vol. 34, Supp., p. 119-26 (2001).

Wu, J. et al., "Transmural Reentry During Acute Global Ischemia and Reperfusion in Canine Ventricular Muscle," *Am J Physical Circ Physiol*, vol. 280, p. H2717-25 (2001).

\* cited by examiner

ISCHEMIA DETECTION BASED ON CARDIAC CONDUCTION TIME

FIELD

The invention relates to cardiac health and, more particularly, to techniques for detection of myocardial ischemia.

BACKGROUND

Myocardial ischemia, a leading cause of mortality, involves oxygen starvation of the myocardium. Myocardial ischemia can lead to myocardial infarction if left untreated. Early detection of myocardial ischemia provides the opportunity for a wide range of effective therapies such as revascularization, neural stimulation, and drug delivery to reduce cardiac workload or improve cardiac circulation. Unfortunately, many episodes of myocardial ischemia do not cause excessive pain or other noticeable warning signs, and often go undetected.

An electrocardiogram (ECG) or electrogram (EGM) presents a PQRST waveform sequence that characterizes the cyclical cardiac activity of a patient. The ST segment, also associated with the repolarization of the ventricles, is typically close in amplitude to the baseline, i.e., isoelectric amplitude of the signal sensed in the TP or PQ segments. During episodes of myocardial ischemia, the ST segment amplitude often deviates from the baseline. Accordingly, deviation in the ST segment is often used to identify an occurrence of myocardial ischemia. Hence, an implantable medical device may be equipped with an ischemia detector that indicates an ischemic condition based on elevation or depression of the ST-segment relative to a baseline. Alternatively, the ischemia detector may rely on a measure of heart activity or patient workload.

Unfortunately, the use of the ST segment as an indicator of ischemia can be unreliable. The ST segment may deviate from the baseline due to other factors, causing false indications of myocardial ischemia. For example, the ST segment may deviate from the baseline due to changes in the overall PQRST complex, possibly caused by axis shifts, electrical noise, cardiac pacing stimuli, drugs and conduction aberrancy that distorts the PQRST complex. In addition, the occurrence of cardiac ischemia may not manifest as changes in the ECG or EGM signals. Consequently, the reliability of the ST segment as an indicator of myocardial ischemia can be unacceptably low.

U.S. Pat. No. 6,128,526 to Stadler et al. describes an ischemia detector that observes variation in the ST segment to identify an ischemic condition. To improve reliability, the detector is designed to filter out ST segment variations caused by factors other than ischemia, such as axis shift, electrical noise, cardiac pacing, conduction aberrancy, and other distortions in the overall PQRST complex. Nevertheless, the sensitivity and specificity of ischemia detection based on observation of ST-segment changes is suboptimal. Accordingly, there continues to be a need for a simplified system capable of automatically and reliably detecting myocardial ischemia.

SUMMARY

The invention is directed to techniques for monitoring disease-related changes in myocardial substrate with an emphasis on more reliable detection and treatment of myocardial ischemia. In particular, the techniques involve detection and analysis of changes in electrical conduction velocity within the heart to monitor changes in the condition of the heart muscle and thereby indicate possible ischemia. Conduction velocity slows considerably when oxygen supply to the heart is reduced. Thus, analysis of electrical conduction velocity or, alternatively, conduction time between two fixed electrodes in contact with the heart, can be used to verify the occurrence of myocardial ischemia in a more reliable manner. Accordingly, in the text below, the term "conduction velocity" may broadly refer to representation of electrical propagation as measured by conduction time between two individual fixed electrodes. Alternatively, the conduction time may be measured between two pairs of fixed electrodes, e.g., in a bipolar electrode arrangement.

The conduction time may be monitored between electrodes positioned in or on the left and right ventricles of the heart. The electrodes may be endocardial or epicardial electrodes. In some cases, one of the electrodes may be endocardial and another electrode may be epicardial. In general, the techniques may involve launching a wave front from a first electrode and sensing the arrival of this wave front at a second electrode to assess average conduction time across the heart tissue. More particularly, a stimulus that initiates myocardial depolarization is delivered to the first electrode or pair of electrodes. The second electrode or pair of electrodes then senses the arrival of the wave front as local cardiac depolarization. The time between launching the wave front at the first electrode(s) and sensing the local cardiac depolarization at the second electrode(s) provides an indication of conduction velocity and, hence, the state of the cardiac tissue. Disease-related changes in myocardial substrate, e.g., manifesting in myocardial ischemia, can be detected based on changes in this time.

The techniques for analysis of conduction velocity may be implemented within an implantable medical device. A change in conduction time represents a change in conduction velocity, and may be used as an independent mode for verification of ischemia. Alternatively, changes in conduction time may be considered in combination with other measurements, such as ST segment deviation, to detect ischemia. As a further alternative, the conduction time may be considered in combination with a patient activity level, e.g., as indicated by an accelerometer signal, to distinguish changes in conduction time that occur with changes in activity level from those that occur with ischemia. The change in conduction time may be compared to a threshold for detection of ischemia. In addition, the rate of change in conduction time may be analyzed to distinguish ischemia-induced changes from anomalous changes that may be caused by other factors.

In one embodiment, the invention provides a method comprising detecting cardiac conduction time, and indicating myocardial ischemia based on the detected conduction time.

In another embodiment, the invention provides a device comprising a detector to detect cardiac conduction time, and indicate myocardial ischemia based on the detected conduction time.

In an added embodiment, the invention provides a device comprising means for detecting cardiac conduction time, and means for indicating myocardial ischemia based on the detected conduction time.

In a further embodiment, the invention provides a method comprising launching a first stimulation wave front from a first ventricular chamber, sensing a first local cardiac depolarization in a second ventricular chamber, detecting a first time between launching the first wave front and sensing the first local cardiac depolarization, launching a second stimulation wave front from the second ventricular chamber, sensing a second local cardiac depolarization in the first ventricular chamber, detecting a second time between launching the second wave front and sensing the second local cardiac depolarization, and indicating myocardial ischemia based on the first time and the second time.

In another embodiment, the invention provides a device comprising means for launching a first stimulation wave front from a first ventricular chamber, means for sensing a first local cardiac depolarization in a second ventricular chamber, means for detecting a first time between launching the first wave front and sensing the first local cardiac depolarization, means for launching a second stimulation wave front from the second ventricular chamber, means for sensing a second local cardiac depolarization in the first ventricular chamber, means for detecting a second time between launching the second wave front and sensing the second local cardiac depolarization, and means for indicating myocardial ischemia based on the first time and the second time.

The invention may provide a number of advantages. In accordance with the invention, detection of changes in electrical conduction velocity within the heart, e.g., via measurement of conduction time, may provide a more reliable indication of an ischemic episode. In particular, the invention may be useful in increasing the specificity of ischemia detection, generally avoiding false indication of ischemic events due to axis shifts, electrical noise, cardiac pacing stimuli, high sinus or tachycardia rates, or other factors that undermine the effectiveness of existing techniques such as ST segment deviation analysis. The invention may also be useful in increasing the sensitivity of ischemia detection by detecting some ischemia episodes that are not manifested in ECG or EGM waveforms. In addition, in some embodiments, the invention can be useful in quantifying a degree or severity of ischemic tissue according to the amount and/or rate of change in conduction time.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

DETAILED DESCRIPTION

Figure 1:
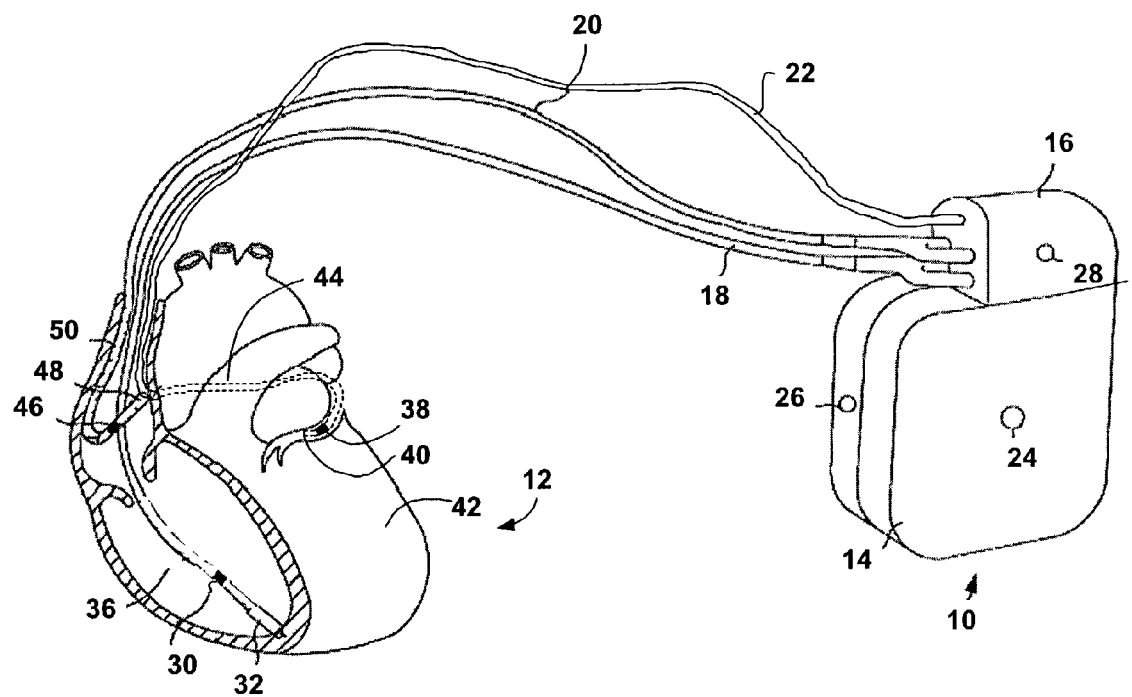
FIG. 1 is a diagram illustrating an exemplary implantable medical device in association with a heart.

FIG. 1 is a diagram illustrating an exemplary implantable medical device (IMD) 10 in association with a human heart 12. IMD 10 may be dedicated to monitoring of heart 12, or integrate both monitoring and therapy features, as will be described. In accordance with the invention, IMD 10 is configured to detect cardiac conduction velocity, via measurement of conduction time, and detect myocardial ischemia based on the detected conduction time. Using conduction time, IMD 10 detects changes in the state of heart 12, and thereby obtains an indication of heart tissue conditions suggestive of myocardial ischemia within the heart 12.

When a change in cardiac conduction time reveals ischemic conditions, IMD 10 indicates an ischemic episode. Conduction velocity across cardiac muscle tends to decrease significantly when oxygen supply to the heart is reduced. At the same time, conduction time tends to increase. Consequently, the conduction time between two fixed electrodes can provide a good indication of cardiac ischemia. In some embodiments, IMD 10 may monitor both conduction time changes and other parameters such as ST segment deviation from a baseline and patient activity level to identify an ischemic episode.

If ischemia is detected, IMD 10 may deliver appropriate therapy to alleviate its effects. The therapy may include drug delivery, electrical stimulation, or both. In addition, the therapy may be delivered directly by IMD 10 or by other devices in response to indication of ischemia by the IMD. In addition, according to some embodiments, IMD 10 may be configured to determine the degree of severity of the ischemic condition, providing more specific information that may be useful in selection of particular therapies. For example, IMD 10 may quantify a change in conduction time and estimate the extent of ischemia as a function of the quantity. In this case, IMD 10 may select a particular therapy, or select a level of stimulation or drug delivery associated with the therapy, according to the estimated degree of severity of the ischemic episode.

As shown in FIG. 1, IMD 10 may be generally flat and thin to permit subcutaneous implantation within a human body, e.g., within upper thoracic regions or the lower abdominal region. IMD 10 may include a hermetically sealed housing 14 having a connector block assembly 16 that receives the proximal ends of one or more cardiac leads for connection to circuitry enclosed within the housing. In the example of FIG. 1, connector block assembly 16 receives three cardiac leads. In particular, connector block assembly 16 receives a right ventricular endocardial lead 18, a left ventricular epicardial lead 22, and a right atrial endocardial lead 20. In addition, housing 14 may function as an electrode, along with a set of electrodes 24, 26, 28 provided at various locations on the housing or connector block assembly 16.

Ventricular leads 18, 22 may include, in some embodiments, pacing electrodes and defibrillation coil electrodes (not shown) in the event IMD 10 is configured to provide pacing, cardioversion and defibrillation. In addition, ventricular leads 18, 22 may deliver pacing stimuli in a coordinated fashion to provide biventricular pacing and cardiac resynchronization. Electrodes 24, 26, 28 may form a variety of sensing pairs with electrodes carried by leads 18, 20, 22 to obtain different sets of desired EGM data for heart 12.

To detect cardiac conduction time, in accordance with the invention, right ventricular lead 18 includes a signal transmitting electrode 32 adjacent a distal end of the right ventricular lead within right ventricle 36 of heart 12. Right ventricular lead 18 may carry other sense or stimulation electrodes, such as electrode 30 shown in FIG. 1. In addition, left ventricular lead 22 includes a signal sensing electrode 38 adjacent a distal end 40 of the left ventricular lead. Electrodes 32, 38 transmit and sense electrical potentials in relation to a reference electrode, which may be carried on IMD 10, e.g., as part of housing 14. Alternatively, the reference electrode may be provided as part of a bipolar electrode configuration carried by the respective lead 18, 22. Left ventricular lead 22 may be deployed to contact left ventricle 42 via the coronary sinus and coronary vein 44. Atrial lead 20 may be provided to permit atrial sensing, and may include an electrode 46 adjacent a distal end 48 of the right atrial lead within right atrium 50.

In operation IMD 10 drives signal transmitting electrode 32 via right ventricular lead 18 to apply a stimulation wave front to right ventricle 36. The wave front is selected to have an amplitude and pulse width sufficient to initiate myocardial depolarization in right ventricle 36. Sensing electrode 38 senses a localized cardiac depolarization in left ventricle 42 upon propagation of the depolarization wave front from right ventricle 36, and communicates the sensed signal to IMD 10 via left ventricular lead 22. IMD 10 may include sensor circuitry to process the received signal. In addition, IMD 10 may include detector circuitry to determine a conduction time based on the time delay between application of the stimulation wave front in right ventricle 36 and sensing of the local depolarization in left ventricle 42. In this manner, the detection circuitry permits detection of myocardial ischemia based on a change in the detected conduction time.

The cardiac conduction time varies as a function of the condition of tissue within heart 12, and provides an indication of ischemia. The ischemic condition can be treated, e.g., by intervention of a physician or in an automated manner. For example, upon detection of the ischemic condition, IMD 10 may activate an alarm. Alternatively or in addition to alarm activation, IMD 10 may select a therapy and coordinate the delivery of the therapy by IMD or some other device. In addition, in the event the therapy involves electrical stimulation, the amplitude, frequency, or pulse width of stimulating current can be controlled according to the indicated degree of ischemia to achieve an optimum therapeutic effect. As a further alternative, determination of the severity of ischemic tissue can be used to choose other types of therapy such as drug delivery, as well as types, dosages and durations of drug delivery.

Figure 2:
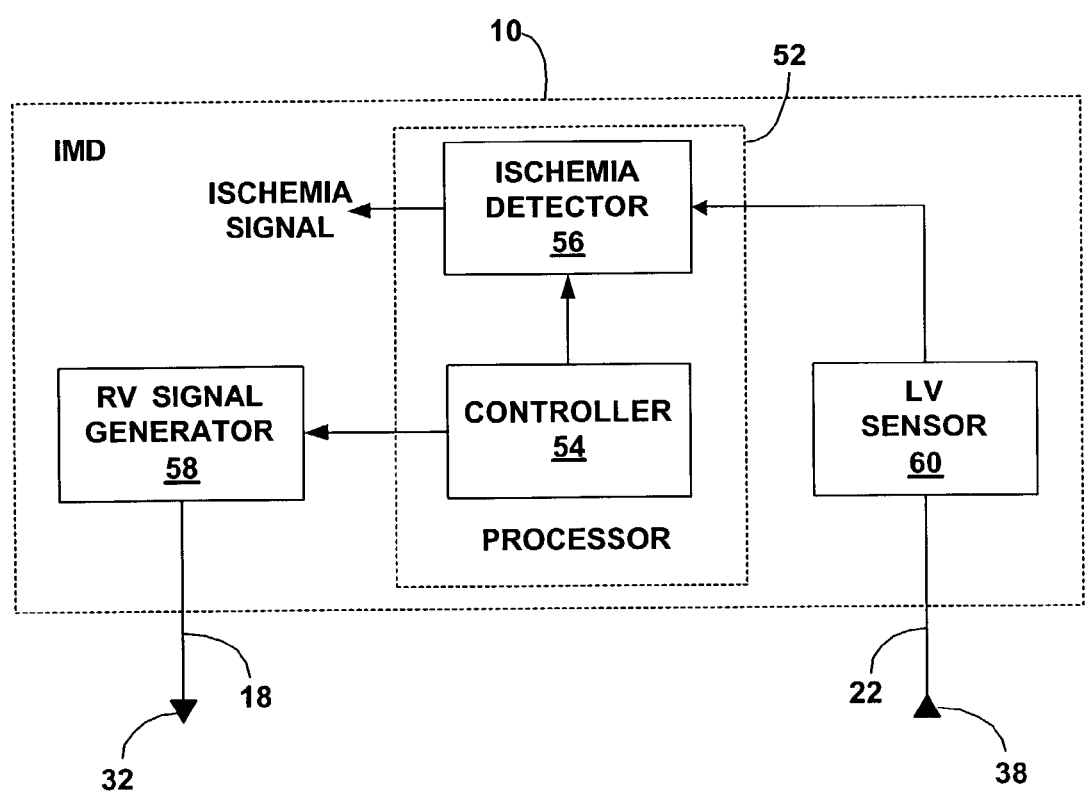
FIG. 2 is a block diagram illustrating a device for detection of ischemia.

FIG. 2 is a block diagram illustrating an IMD 10 configured for detection of ischemia based on heart tissue conduction time, in accordance with the invention. As shown in FIG. 2 device 10 may include a processor 52 that controls the application of the stimulation wave front in right ventricle 36 and sensing of a localized depolarization in left ventricle 42 to evaluate cardiac conduction time across tissue between electrodes within the right and left ventricles 36, 42 of heart 12. Processor 52 may be realized by a microprocessor, digital signal processor, ASIC, FPGA, or other integrated or discrete logic circuitry programmed or otherwise configured to provide functionality as described herein.

Processor 52 may function to provide, for example, a controller 54 and an ischemia detector 56. Controller 54 and ischemia detector 56 may be programmable features or functional blocks of processor 52. Controller 54 controls the operation of right ventricular signal generator circuitry 58. Signal generator circuitry 58, in response to a control signal from controller 54, launches a stimulation wave front into right ventricle 36 via signal transmitting electrode 32 of right ventricular lead 18.

For patients with little or no intrinsic rhythm, such as patients with second or third degree AV conduction block, that are paced for a majority or all of the time, the stimulation wave front can be readily coordinated with pacing pulses. In particular, right ventricular pacing pulses may be used as the stimulation wave front that initiates a myocardial depolarization in right ventricle 36, which then propagates across the cardiac tissue to cause a local depolarization in left ventricle 42. In patients with normal sinus activity, overdrive pacing slightly above the sinus rate can be performed at regular intervals to obtain the conduction times. The time interval for measurements can be a programmable parameter of IMD 10, which may be patient specific and set at the discretion of the physician.

Left ventricular sensor circuitry 60, coupled to left ventricular lead 22, captures the sensed depolarization received at measurement electrode 38.

Sensor circuitry 60 may amplify, condition and digitize the depolarization signal, and provide the signal in digital form to ischemia detector 56. In some embodiments, sensor circuitry 60 may merely present to ischemia detector 56 a timing signal indicative of the arrival of the depolarization at measurement electrode 38 for comparison to the transmission time of the stimulation wave front at transmitting electrode 32.

As an alternative to transmission of the stimulation wave front via right ventricular lead 18 and sensing via left ventricular lead 22, the left ventricular lead could be equipped with a set of bipolar epicardial electrodes. In this case, conduction time can be measured at the surface of the left ventricle 42 by transmitting a stimulation wave front between the bipolar electrodes of left ventricular lead 22. The bipolar electrodes may be disposed at different axial positions along the length of left ventricular lead 22, and may be approximately 1 to 2 cm apart from one another.

An epicardial arrangement may be particularly effective in identifying the onset of ischemia because the effect of ischemia is first felt in the epicardial layers of the cardiac tissue. As a result, changes in conduction time between a pair of epicardial electrodes carried by left ventricular lead 22 may serve to provide an early warning of ischemia. Moreover, proximity of a pair of left ventricular epicardial electrodes to the left anterior descending (LAD) and circumflex arteries, the two most commonly occluded arteries, would make such a configuration particularly sensitive to ischemia detection.

In operation, ischemia detector 56 tracks the time the stimulation wave front was applied by right ventricular lead 18 and the time the resulting depolarization was sensed by left ventricular lead 22 to determine the conduction time across the heart tissue between right and left ventricles 36, 42 of heart 12. As ischemia sets in, and the conduction velocity progressively decreases, the conduction times between the two electrodes on leads 18, 22 will increase.

Ischemia can be detected when the conduction time is longer than a threshold value. The threshold value may be a nominal value derived from a typical implanted cardioverter-defibrillator device (ICD) population of patients.

Alternatively, the threshold value may be independently adjusted and set for a given patient as desired by the attending physician. For diagnosis purposes, the more recent values of the conduction time, e.g., with a time and date stamp, as well as other information, may be stored in a memory associated with IMD 10 along with the most recent arrhythmia to facilitate diagnosis of any association between the onset of ischemia and arrhythmia episodes.

Over a period of time, processor 52 may collect a series of conduction time samples as a function of the measured conduction time. With each sample, ischemia detector 56 compares the conduction time to a baseline conduction time evaluated in one or more previous samples to identify a change in conduction time. The baseline conduction time may be updated over time. For example, the baseline conduction time may represent a mean or median conduction time over a period of n preceding samples.

When the change in conduction time exceeds a predetermined threshold, ischemia detector 56 indicates an ischemic condition within heart 12 and generates an ischemia,signal. The change in conduction time may be measured based on a single sample, or based on the mean or median conduction time change over a series of samples. The ischemia signal may be used to drive selection and delivery of one or more therapies.

Figure 3:
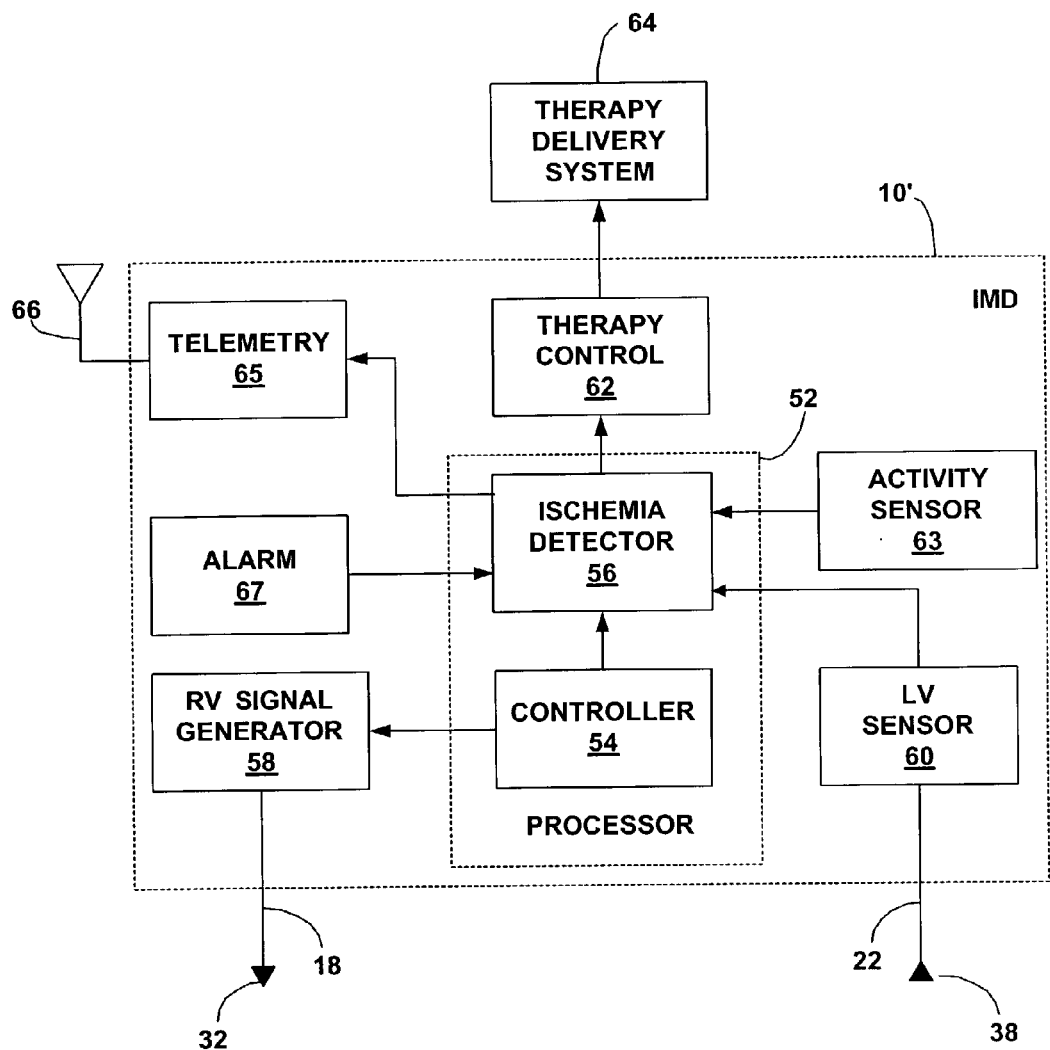
FIG. 3 is a block diagram illustrating a device for detection of ischemia and delivery of therapy.

FIG. 3 is a block diagram illustrating an IMD 10' configured for detection of ischemia and delivery of therapy. IMD 10' of FIG. 3 corresponds substantially to IMD 10 of FIG. 2, but further includes both a therapy control circuit 62 that drives a therapy delivery system 64, and a telemetry circuitry 65 that drives an antenna 66. IMD 10 also may include an activity level sensor 63 to indicate a level of physical activity of a patient in which the IMD is implanted. Activity level sensor 63 may include, for example, an accelerometer. When ischemia detector 56 detects a change in conduction time that exceeds a threshold, it transmits an ischemia signal to therapy control circuitry 62, which may interact with a-therapy delivery system 64 within IMD 10' or associated with another device, or both.

Therapy delivery system 64 may take the form of a drug delivery system or electrical stimulation system such as a neurostimulation, pacing, cardioversion or defibrillation circuit. For example, in some embodiments, therapy control circuitry 62 may interact with an electrical stimulation therapy device integrated with IMD 10' to deliver pacing, post-extrasystolic potentiation, cardioversion or defibrillation therapy, and also communicate with a drug delivery device that may be implanted or external to deliver drug therapy to the patient. In addition, telemetry circuitry 65 may alert an external monitoring system by wireless communication via antenna 66. IMD 10' also may include internal alarm circuitry 67 that is responsive to the ischemia signal produced by ischemia detection circuitry 56.

In addition, in some embodiments, ischemia detector 56 of IMD 10' as described herein may include electrocardiogram signal analysis circuitry for identifying deviation of the ST segment of the electrocardiogram as an indication of ischemia. In this manner, IMD 10' may analyze both conduction time and ST segment deviation to detect ischemia. If IMD 10' detects an ST segment deviation greater than a given ST threshold, for example, in combination with a conduction time change that exceeds another threshold, IMD 10' may identify an ischemic episode. In this manner, the conduction time change can provide confirmation that the ST segment deviation is due to an ischemic condition, rather than an anomalous ST segment deviation caused by factors other than ischemia. Alternatively, the sensitivity to ischemia could be increased by identifying an ischemic episode when either the conduction time or an ST-segment deviation are detected.

Based on the amount of conduction time change, IMD 10 also may quantify the severity of the ischemic condition. In some embodiments, the ischemia signal transmitted by ischemia detector 60 may specify selection of a particular type of therapy, e.g., drug delivery and/or electrical stimulation, as well as the level, dosage, amplitude, and duration of the therapy, based on the indications of the severity of the ischemic condition determined from the amount of conduction time change.

Telemetry circuitry 65, as discussed above, communicates an indication of the ischemic condition to an external device via antenna 66.

Thus, the indication may be a wireless, radio frequency message that indicates an ischemic condition and, in some embodiments, the severity of the ischemic condition. In addition, IMD 10' itself may have an audible alarm within alarm circuitry 67 that notifies the patient when an ischemic episode is occurring. The external device that receives the wireless message may be a programmer/output device that advises a physician or other attendant of the ischemic condition, e.g., via a display or a visible or audible alarm. Also, the ischemic events may be stored in memory in the external device, or within the IMD 10', for review by a physician.

The components of IMD 10, with the exception of leads 18, 22, may be housed in a common housing such as that shown in FIG. 1. Alternatively, portions of IMD 10' may be housed separately. For example, therapy delivery system 64 could be integrated with IMD 10' or provided in a separate housing, particularly where the therapy delivery system includes drug delivery capabilities. In this case, therapy control circuit 62 may interact with therapy delivery system 64 via an electrical cable or wireless link.

Figure 4:
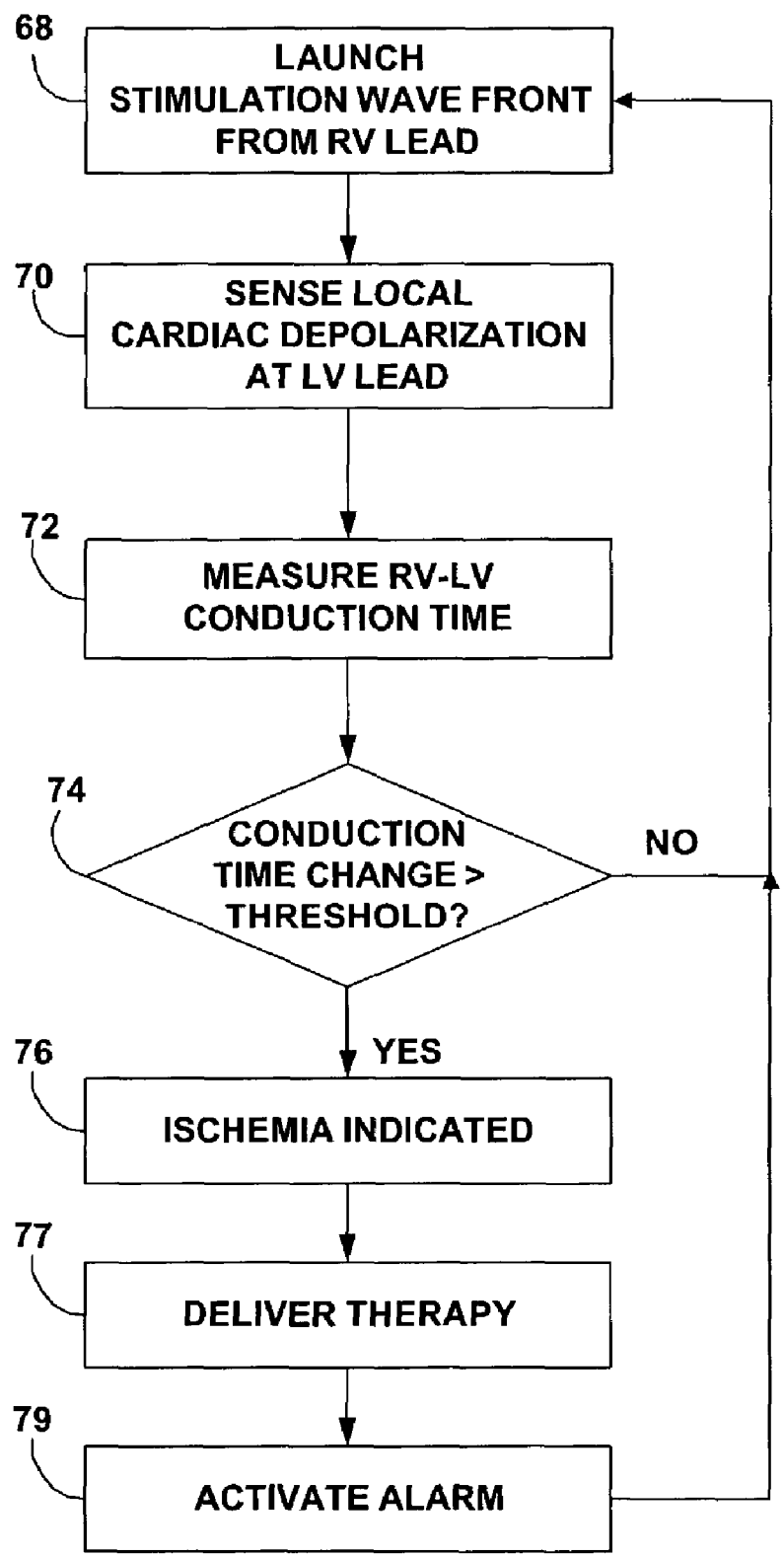
FIG. 4 is a flow diagram illustrating a technique for detection of ischemia based on cardiac conduction time.

FIG. 4 is a flow diagram illustrating a technique for detection of ischemia based on conduction time. In general, the process may include launching a stimulation wave front from the right ventricular lead 18 (68), detecting a local cardiac depolarization at the left ventricular lead 22 (70), and measuring the conduction time between the right and left ventricular leads 18, 22 (72). The conduction time may be determined based on the time required for the depolarization initiated by the stimulation wave front to propagate across the heart tissue from right ventricular lead 18 to left ventricular lead 22 and cause a depolarization in left ventricle 42.

In the example of FIG. 4, the stimulation wave front is transmitted from the right ventricular endocardial lead 18, with the resulting depolarization being sensed by the left ventricular epicardial lead 22. However, an opposite arrangement may be used in which the stimulation wave front is transmitted from the left ventricular epicardial lead 22, and the resulting depolarization is, sensed by the right ventricular endocardial lead 18. Moreover, in some embodiments, both leads may be endocardial leads, or both leads may be epicardial leads.

The process involves determining conduction time and then comparing the conduction time to a threshold conduction time (74). More specifically, in certain embodiments, the process compares a change in the conduction time to a change threshold. Again, the change in conduction time may be determined by comparing a mean or median conduction time over a series of samples to a mean or median conduction time for a preceding series of samples. If the change in conduction time exceeds the threshold (74), the process indicates ischemia (76). In some embodiments, the comparison of the conduction time to a threshold may be accompanied by analysis of ST segment deviation or other parameters that may also be indicative of an ischemic episode. Upon detection of an ischemic episode, the process further may involve delivery of therapy (77) and activation of an alarm (79).

Figure 5:
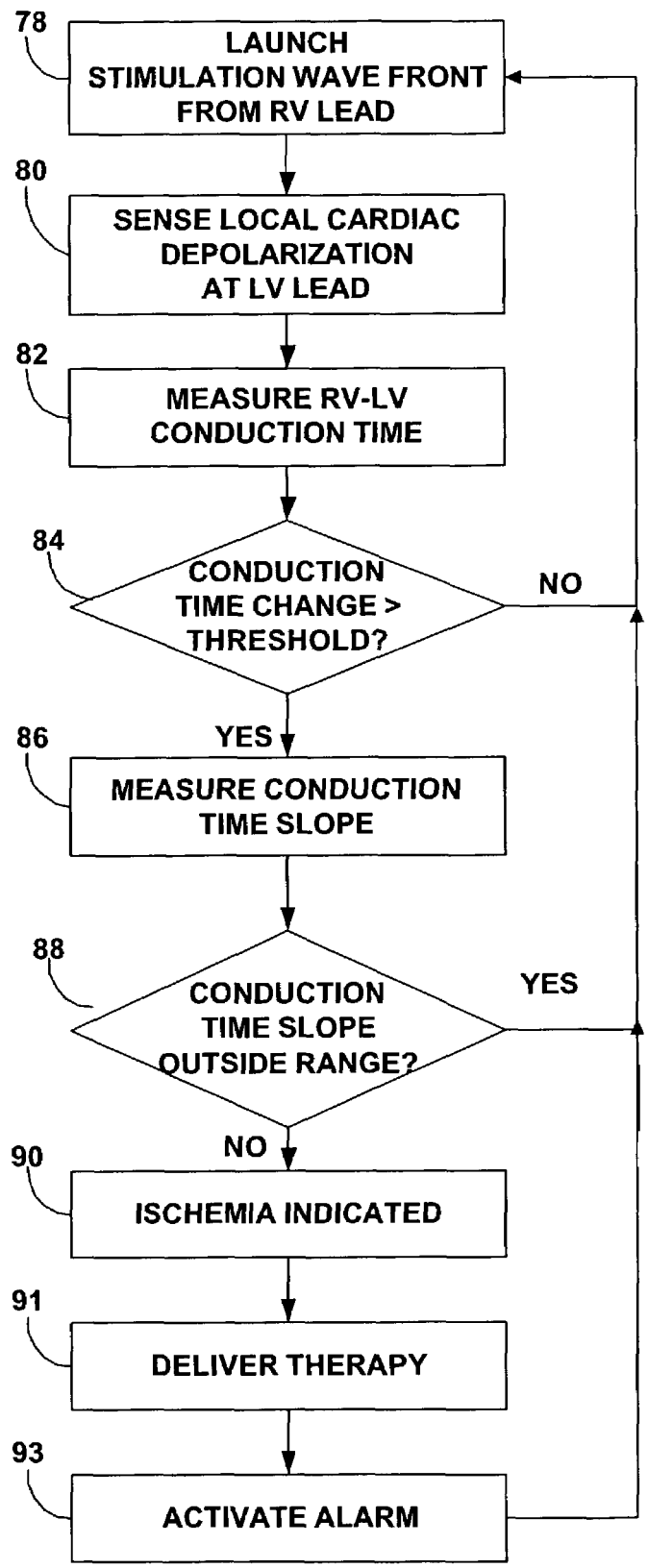
FIG. 5 is a flow diagram illustrating another technique for detection of ischemia based on cardiac conduction time.

FIG. 5 is a flow diagram illustrating another process for detection of ischemia based on conduction time. In the example of FIG. 5, the process involves launching a stimulation wave front from the right ventricular lead 18 (78), detecting the resulting depolarization at the left ventricular lead 22 (80), and measuring the conduction time between the right and left ventricular leads 18, 22 (82). Again, the stimulation wave front alternatively may be transmitted from the left ventricular lead 22, with the depolarization sensed at the right ventricular lead 18, and the process is subject to variation in the endocardial or epicardial arrangement of the leads. The process next determines whether the conduction time change is greater than a given threshold (84). In the example of FIG. 5, the process may rely on a static threshold that does not take into account the conduction time associated with previous samples.

If the conduction time change is greater than an applicable threshold (84), the process next measures the slope of the conduction time change (86). The slope of the conduction time change over time can serve to distinguish changes that are indicative of ischemia from spurious changes that may arise due to other factors. For example, many non-ischemic conditions such as drug therapy, changes in electrolyte concentrations, temperature changes, progression of disease, and the like may influence myocardial conduction time very slowly. Conversely, fusion of stimulated and intrinsic depolarization wave fronts, conduction aberrancy, electrode motion or dislodgement, and the like may influence the measured conduction time very rapidly. For these reasons, the rate of change (i.e., slope) of the conduction time over time may serve to distinguish among various factors influencing conduction time.

To improve the specificity of ischemic detection based on conduction time, the process may be configured to exclude non-ischemic etiology of changes in conduction time by accepting only specific rates of change of the conduction time as being indicative of ischemia. If the conduction time slope falls outside of a desired range (88), i.e., the rate of change is too slow or too fast, the process ignores the conduction time change and does not indicate an ischemic episode. If the conduction time slope is within the desired range, however, the process indicates ischemia (90). In this case, IMD 10 may direct delivery of therapy (91) and activation of an alarm (93).

An increase in conduction time that is caused by ischemia will tend to follow a known time course, typically resulting in a fifty percent increase in conduction time over a period of one to ten minutes. An increase in conduction time that occurs faster than such a rate generally is not caused by ischemia. Rather, the likely cause of the increase in conduction time will be a conduction aberrancy, electrode motion or dislodgement, or conduction block in a section of the myocardium that is refractory. To avoid the possibility of encountering refractive myocardium, it may be desirable to avoid transmission of the stimulation wave front prematurely or immediately following a premature ventricular contraction.

An increase in conduction time that occurs over a time period longer than approximately ten minutes also generally is not caused by ischemia.

Instead, the likely cause of slow changes in conduction time are changes in electrolytes, medications or progression of disease. Accordingly, it may be desirable to exclude changes in conduction time that are too slow or too fast to be caused by ischemia, as served by the slope comparison (88).

To exclude slow, drifting changes in conduction time, a baseline conduction time, i.e., a normal expected conduction time, may be allowed to change slowly over time. A baseline conduction time may be established over a series of conduction time measurement samples. Observation of an ischemic change then becomes an observation of a change in conduction time relative to the adaptive baseline conduction time. To exclude fast, sudden changes in conduction time, an adaptive expected range of conduction times can be established. The expected range could be composed, for example, of an adaptive mean of conduction time+/− an adaptive estimate of the variability of conduction times. Measurements of conduction time that occur outside of the expected range may be excluded as outliers. If consecutive measurements are consistently excluded as outliers, a new expected range of conduction times, based on this new steady state value, can be established.

Figure 6:
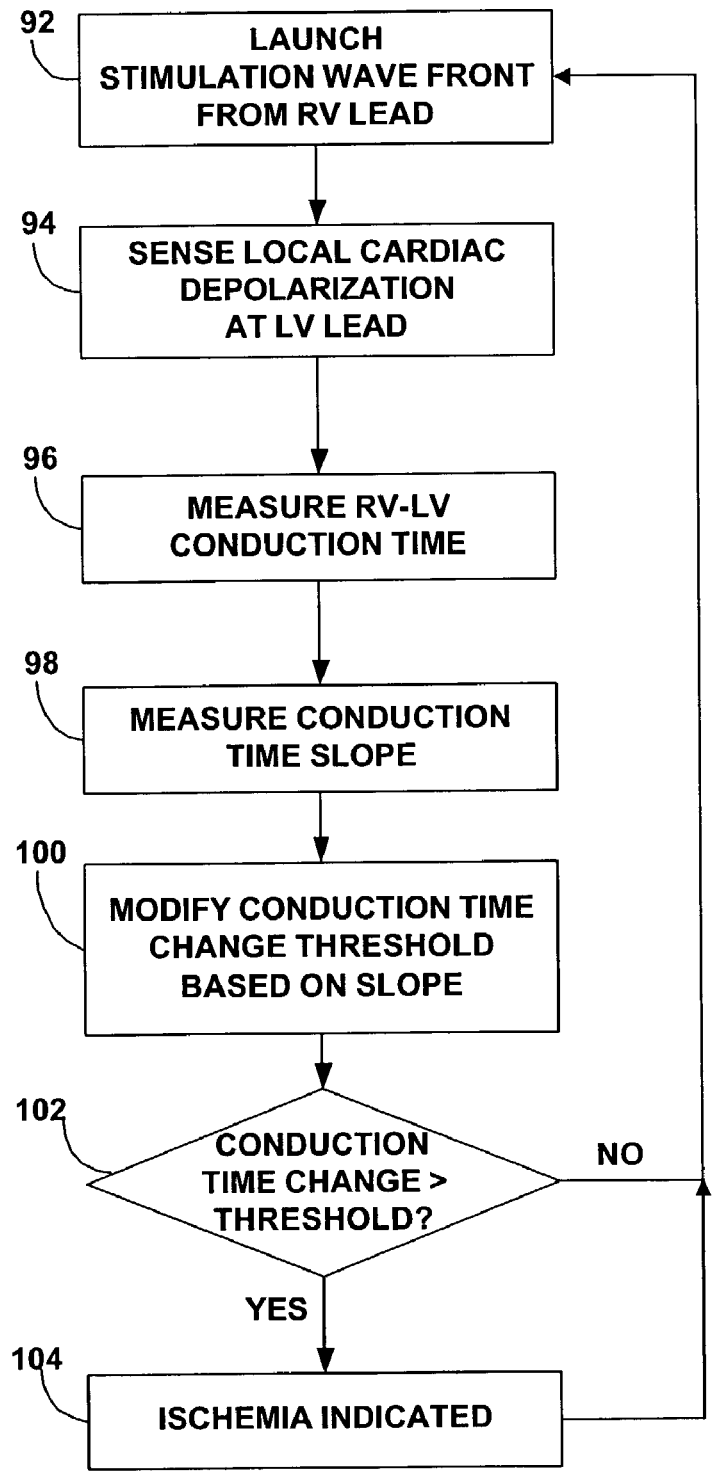
FIG. 6 is a flow diagram illustrating a further technique for detection of ischemia based on cardiac conduction time.

FIG. 6 is a flow diagram illustrating a further process for detection of ischemia based on conduction time. The process illustrated in FIG. 6 may correspond substantially to the process of FIG. 5. Instead of using a static conduction time change threshold, however, the process makes use of a dynamic conduction time change threshold that varies as a function of recent conduction time samples. Accordingly, as shown in FIG. 6, the process involves launching a stimulation wave front from the right ventricular lead 18 (92), detecting arrival of the resulting depolarization at the left ventricular lead 22 (94), and measuring the conduction time between the right and left ventricular leads 18, 22 (96).

The process next determines a slope of the conduction time over a series of recent conduction time samples (98). Based on the slope, the process modifies the threshold value of conduction time change (100). In this manner, the process adapts the threshold value for conduction time change to the rate of change in the measured conduction time. If the measured conduction time changes more rapidly, the process may involve increasing the threshold level of the conduction time change for ischemia detection. If the conduction time changes more slowly, the process may involve decreasing the threshold level of the conduction time change for ischemia detection.

The dynamic threshold serves to adapt the process to changing conditions in the conduction time, and can help to avoid detection of ischemia based on momentary, spurious shifts in conduction time. For example, if the conduction time changes abruptly, the level of the conduction time threshold may be increased to require a larger change. If the conduction time change exceeds the threshold (102), the process detects ischemia (104). In response, IMD 10 may direct delivery of therapy and activation of an alarm (such as alarm 67 in FIG. 3).

Figure 7:
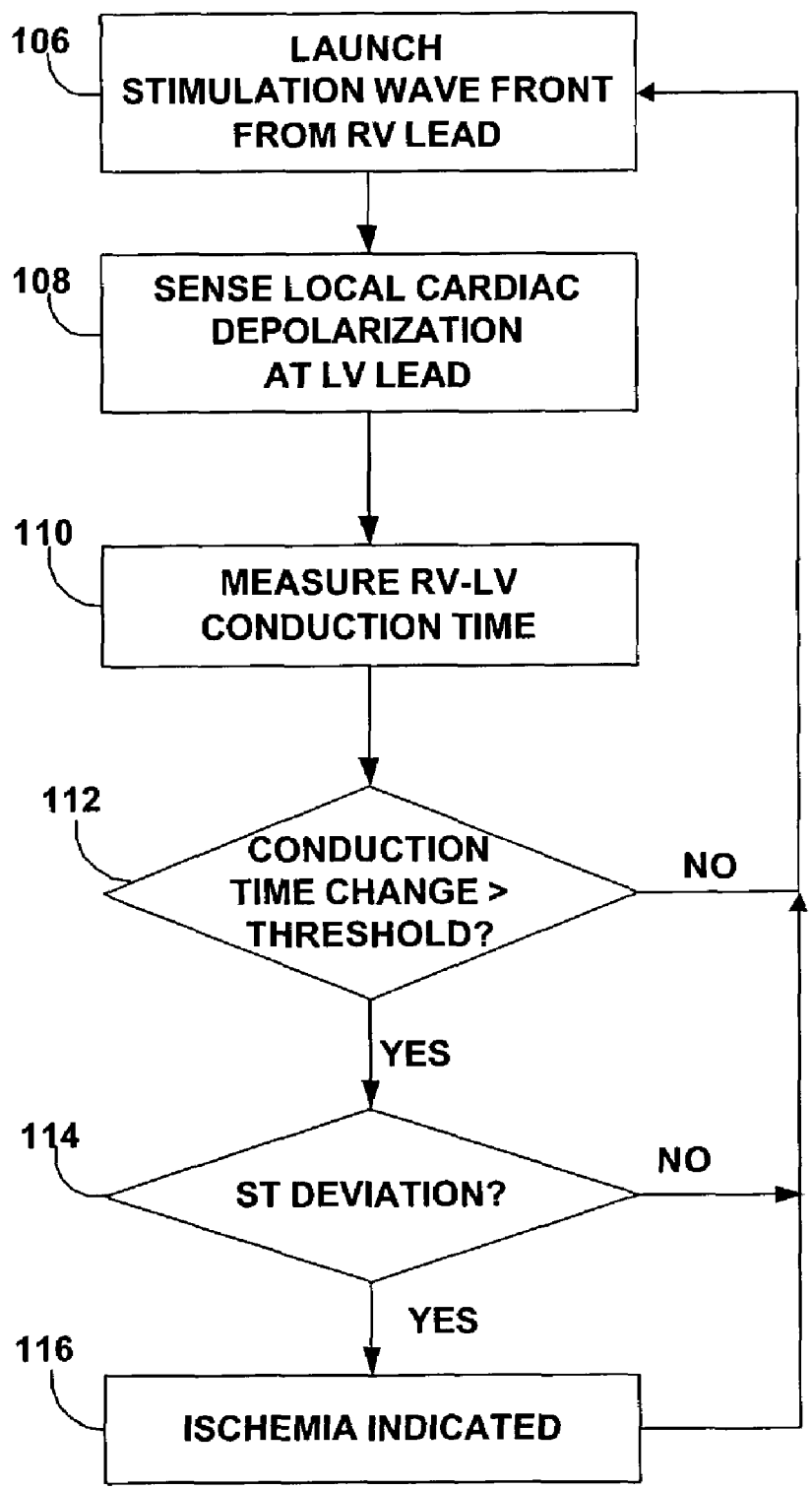
FIG. 7 is a flow diagram illustrating a technique for detection of ischemia based on cardiac conduction time and ST segment deviation.

FIG. 7 is a flow diagram illustrating a process for detection of ischemia based on conduction time and ST deviation. As shown in FIG. 7, the process involves launching a wave front from the right ventricular lead 18 (106), detecting the conducted wave front at the left ventricular lead 22 (108), and measuring the conduction time between the right and left ventricular leads 18, 22 (110). If the conduction time change exceeds an applicable threshold (112), the process analyzes the ST segment to identify ST deviation from isoelectric (114) and thereby corroborate the ischemic condition indicated by the change in conduction time. If ST deviation greater than a particular level exists, the process indicates ischemia (116), and may direct delivery of therapy and activation of an alarm system. In some embodiments, the process of FIG. 7 may be modified such that ischemia is indicated when either the conduction time change exceeds an applicable threshold or ST deviation is encountered. In this manner, ischemia is indicated in response to either criterion such that the ischemia detection process is less selective but more inclusive, and therefore less likely to miss detection of an ischemic episode.

Figure 8:
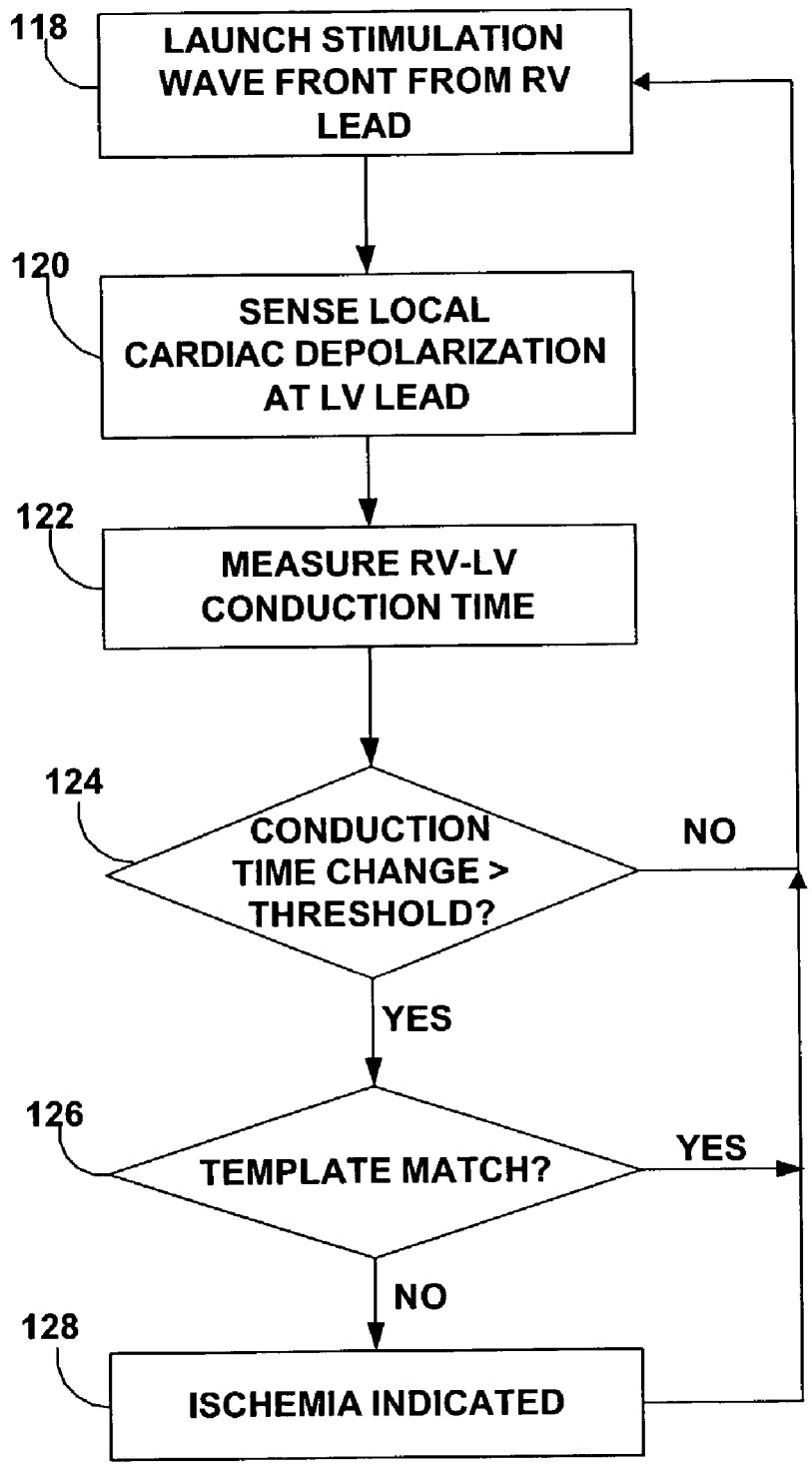
FIG. 8 is a flow diagram illustrating a process for detection of ischemia based on cardiac conduction time and morphology of a waveform used to measure conduction time.

FIG. 8 is a flow diagram illustrating a process for detection of ischemia based on conduction time and waveform morphology. The process of FIG. 8 conforms substantially to the process of FIG. 7. For example, the process of FIG. 8 involves launching a stimulation wave front from the right ventricular lead 18 (118), detecting a resulting depolarization at the left ventricular lead 22 (120), and measuring the conduction time between the right and left ventricular leads 18, 22 (122).

If the conduction time change exceeds an applicable threshold (124), the process further evaluates the morphology of the measured signal waveform, i.e., the sensed depolarization wave form, as an alternative or in addition to ST segment analysis. In particular, processor 52 in IMD 10 may be equipped to perform wavelet analysis of other waveform analysis techniques to analyze the morphology of the depolarization signal or other cardiac waveforms within heart 12. If the morphology matches a template corresponding to a normal morphology (126), the process does not detect ischemia. If the morphology does not match the template (126), i.e., differs significantly from the template, and the conduction time change exceeds the threshold (124), the process indicates ischemia (128).

In this example, analysis of waveform morphology for the depolarization signal received at left ventricular lead 22 serves to corroborate the ischemic condition indicated by the change in conduction time. During ischemia, a broadening of the detected waveform may be expected as the conduction becomes more fractionated. Accordingly, tools such as wavelet analysis may be useful in matching the detected activity against a normal template. A deviation from the template that exceeds a programmed threshold, e.g., waveform width, amplitude, energy, or the like, can be use to signal ischemia or other deleterious changes in the myocardium.

Figure 9:
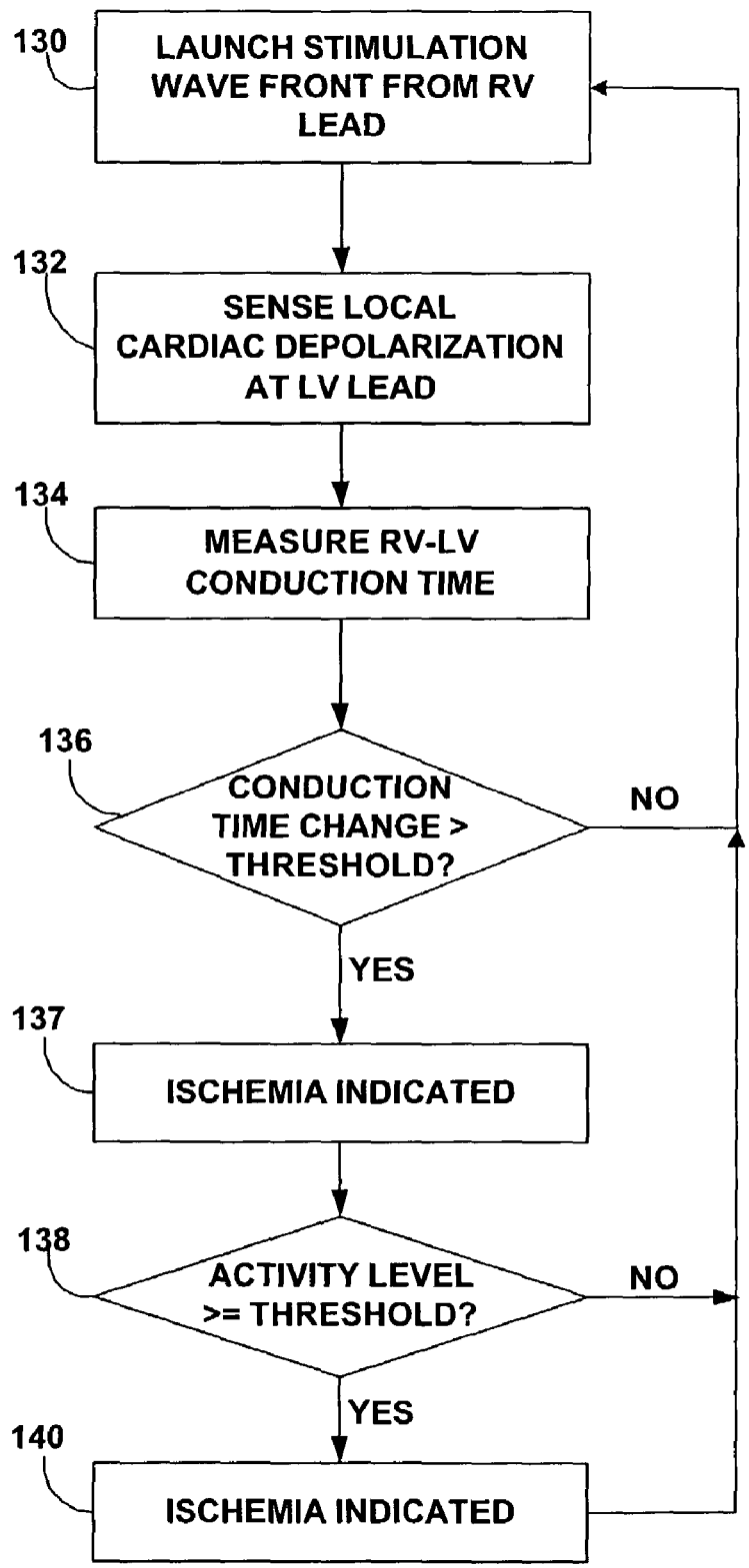
FIG. 9 is a flow diagram illustrating a process for detection of ischemia based on cardiac conduction time and activity level.

FIG. 9 is a flow diagram illustrating a process for detection of ischemia based on conduction time and activity level. As shown in FIG. 9, the process involves launching a stimulation wave front from the right ventricular lead 18 (130), detecting a resulting depolarization at the left ventricular lead 22 (132), and measuring the conduction time between the right and left ventricular leads 18, 22 (134). If the conduction time change exceeds an applicable threshold (136), the process further involves obtaining an activity level (137), e.g., from an activity level sensor 63 (FIG. 3). The activity level can help to distinguish changes in conduction time that occur with changes in activity level from those changes in conduction time that occur with ischemia. In general, if a patient is ischemic, the conduction time should increase with either no change or an increase in activity level. If a patient is not ischemic, however, increases in conduction time should occur only with decreases in activity level. Accordingly, if the activity level is greater than or equal to a threshold (138), the process indicates ischemia (140). If the activity level is less than the threshold, ischemia is not indicated.

Figure 10:
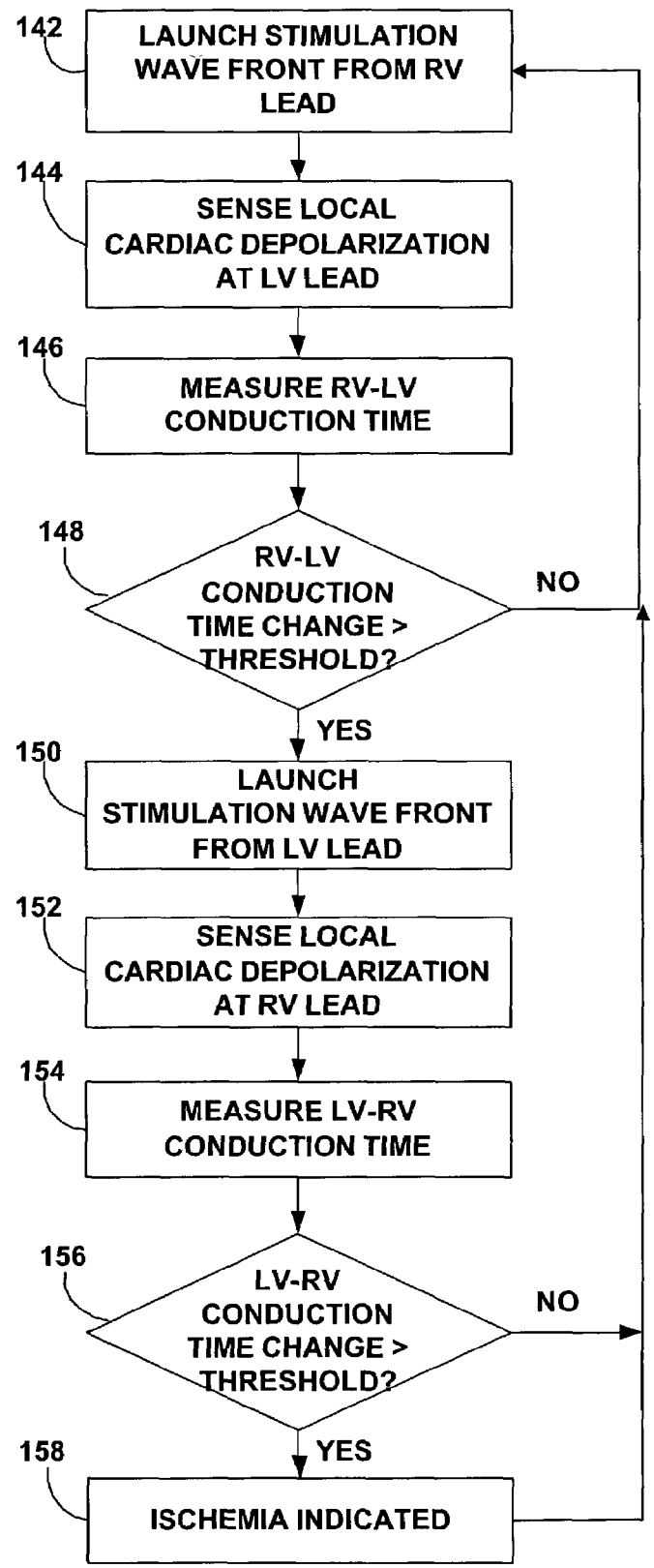
FIG. 10 is a flow diagram illustrating a process for detection of ischemia based on cardiac conduction time between the right ventricle and left ventricle and cardiac conduction time between the left ventricle and the right ventricle.

FIG. 10 is a flow diagram illustrating a process for detection of ischemia based on both conduction time between the right ventricle and left ventricle (RV-LV) and conduction time between the left ventricle and the right ventricle (LV-RV). As shown in FIG. 10, the process involves launching a stimulation wave front from the right ventricular lead 18 (142), detecting a resulting depolarization at the left ventricular lead 22 (144), and measuring the conduction time between the right and left ventricular leads 18, 22 (146). If the RV-LV conduction time change exceeds an applicable threshold (148), the process further involves launching a stimulation wave front from the left ventricular lead 22 (150), detecting a resulting depolarization at the right ventricular lead 18 (152), and measuring the conduction time between the left and right ventricular leads 22, 18 (154). If the LV-RV conduction time change also exceeds an applicable threshold (156), the process indicates ischemia (158).

Figure 11:
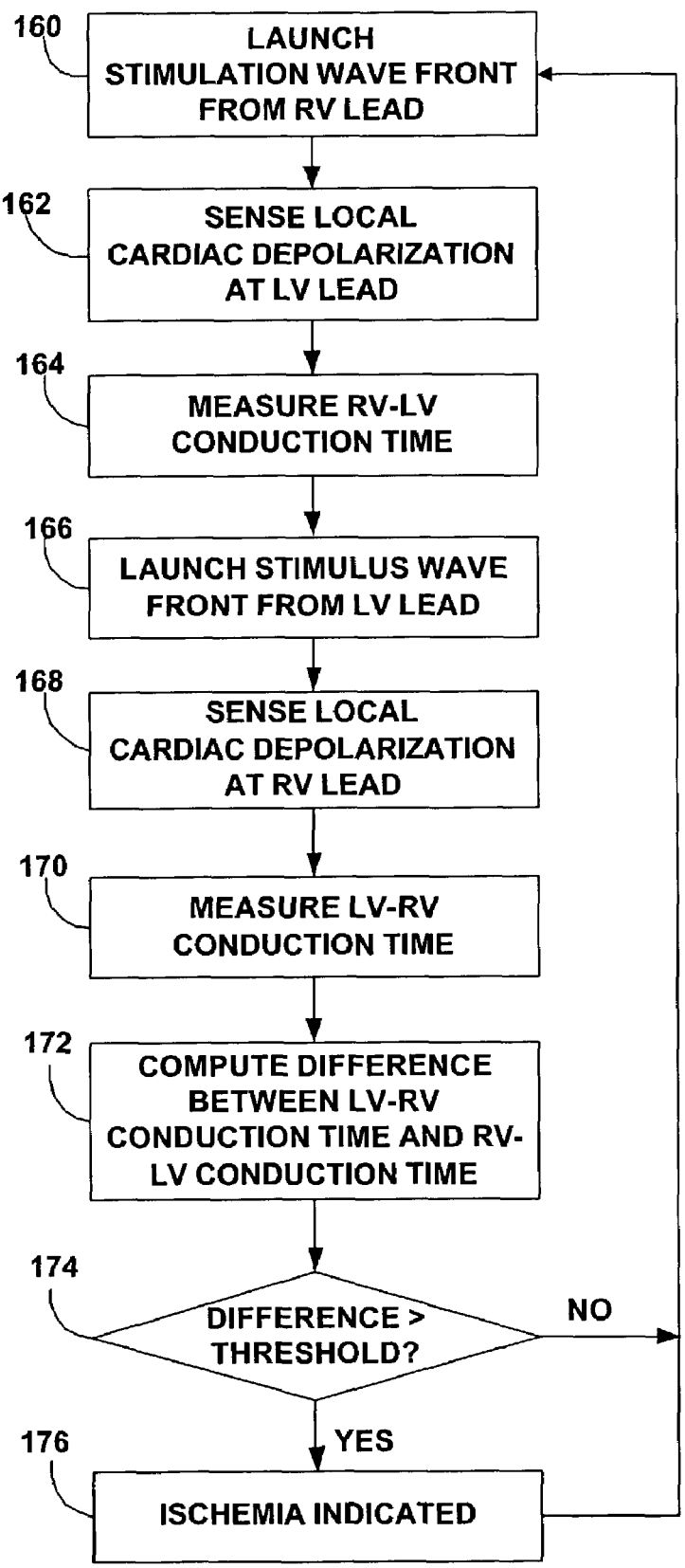
FIG. 11 is a flow diagram illustrating a process for detection of ischemia based on a difference between cardiac conduction time between the right ventricle and left ventricle and cardiac conduction time between the left ventricle and the right ventricle.

FIG. 11 is a flow diagram illustrating a process for detection of ischemia based on a difference between conduction time between the right ventricle and left ventricle and conduction time between the left ventricle and the right ventricle. As shown in FIG. 11, the process involves launching a stimulation wave front from the right ventricular lead 18 (160), detecting a resulting depolarization at the left ventricular lead 22 (162), and measuring the conduction time between the right and left ventricular leads 18, 22 (164). The process further involves launching a stimulation wave front from the left ventricular lead 22 (166), detecting a resulting depolarization at the right ventricular lead 18 (168), and measuring the conduction time between the left and right ventricular leads 22, 18 (170). Upon computing the difference between the LV-RV conduction time and the LV-RV conduction time (172), the process determines whether the difference is greater than a predetermined threshold (174). A significant difference may be an indication of an ischemic condition that has altered the conductive state of the cardiac tissues. Accordingly, if the difference is greater than the predetermined threshold, ischemia is indicated (176).

Additional variations to the embodiments of the invention described herein are also conceivable. For example, as mentioned previously, the stimulation wave front used to measure conduction time may be launched between a variety of lead arrangements, including right endocardial to left endocardial, left endocardial to right endocardial, right endocardial to left epicardial, left epicardial to right endocardial, right epicardial to left epicardial, left epicardial to right epicardial, left bipolar epicardial, and the like.

In addition, the stimulation wave front may be transmitted as part of a pacing pulse or other therapy pulses or as a dedicated measurement pulse.

The stimulation wave front may be transmitted alternatively from the right to the left lead or from the left to the right lead on successive measurement cycles during a single monitoring session to improve sensitivity and specificity for ischemia detection.

As further variations, multiple bipolar electrodes on a single lead may be provided and selected for use in the measurement of conduction time depending on the particular patient's condition, e.g., to be more selectively directed to an area of the heart known to be prone to ischemia. In particular, factors such as location of a previous ischemic condition may affect the location of the optimum transmitting or measurement electrode, or both.

In patients with bi-ventricular pacing, suspension of right ventricular pacing while performing left ventricular pacing could be used to measure conduction time. If appropriate, pacing from the right ventricle and measurement of the depolarization in the left ventricle can be used in some patient populations.

In extreme cases of ischemia, lack of left ventricular or right ventricular capture may occur depending on the location of the ischemic region if the electrode happens to be located inside the ischemic region. In some cases, loss of capture may be used as a rough tool to initially identify the location of an ischemic region.

Further, if the patent has a good sinus rhythm, overdrive pacing from one of the locations for a small number of beats may be desirable so that atrial activity and fusion beats do not confound the conduction time measurements. In patients with regular rhythm, one way to prevent incoming atrial activity from undermining the conduction time measurement may be to perform vagal stimulation, if available, or use other means to temporarily prevent AV conduction.

In many cases, the best location for the right ventricular lead may be determined experimentally, e.g., by performing acute occlusion of an artery that seems most likely to suffer from plaque rupture. In some patients, the right ventricular septal location may be the optimum location for conduction time measurement.

Various embodiments of the invention have been described. These and other embodiments are within the scope of the following claims.

What is claimed is:

1. A method comprising:
    detecting ST segment deviations via a wholly-implantable medical device (IMD);
    detecting patient activity levels via the IMD;
    detecting cardiac conduction time between at least a first pair and a second pair of fully implantable fixed electrodes which are all operatively coupled to an active implantable medical device (IMD), wherein said first pair and said second pair are separate pairs of fully-implantable electrodes; and
    indicating myocardial ischemia based on each one of: (i) changes in conduction time in combination with ST segment deviation, (ii) changes in conduction time in combination with a detected patient activity level, and (iii) the time rate of change of conduction time wherein conduction time is detected between said first pair and said second pair of fully implantable electrodes.

2. The method of claim 1, further comprising:
    launching a stimulation wave front from a pair of first electrodes positioned proximate a first ventricular chamber; and
    sensing a local cardiac depolarization at a pair of second electrodes positioned proximate a second ventricular chamber,
    wherein detecting cardiac conduction time includes detecting a time between launching the wave front and sensing the local cardiac depolarization for each said pair of electrodes.

3. The method of claim 2, wherein the first electrode includes an endocardial electrode positioned within the first ventricular chamber, and the second electrode includes an epicardial electrode positioned on a surface of the second ventricular chamber.

4. The method of claim 2, wherein the first electrode includes an endocardial electrode positioned within the first ventricular chamber, and the second electrode includes an endocardial electrode positioned within the second ventricular chamber.

5. The method of claim 2, wherein the first electrode includes an epicardial electrode positioned on a surface of the first ventricular chamber, and the second electrode includes an epicardial electrode positioned on a surface of the second ventricular chamber.

6. The method of claim 2, wherein the first ventricular chamber is the right ventricular chamber and the second ventricular chamber is the left ventricular chamber.

7. The method of claim 2, wherein the first ventricular chamber is the left ventricular chamber and the second ventricular chamber is the right ventricular chamber.

8. The method of claim 1, further comprising detecting the conduction time using at least one lead associated with an implantable medical device.

9. The method of claim 1, further comprising quantifying a degree of ischemia based on the detected conduction time.

10. A device comprising:
    a wholly-implantable medical device (IMD) including a detector to detect cardiac conduction time between a first pair and a second pair of fully implantable electrodes and a second pair of fully implantable electrodes, and indicate myocardial ischemia based on the detected conduction time of at least one of said first pair and second pair of fully implantable electrodes, wherein said detector includes:
    means for comparing the detected conduction time of said first pair and said second pair to a respective threshold conduction time for said first pair and said second pair;
    means for detecting ST segment deviation disposed within the IMD;
    means for detecting patient activity level disposed within the IMD; and
    means for indicating ischemia, also disposed within the IMD, based on each one of the following: (i) changes in conduction time in combination with ST segment deviation, (ii) changes in conduction time in combination with a detected patient activity level, and (iii) the time rate of change of conduction time wherein conduction time is the detected conduction time between said first pair and said second pair of fully implantable electrodes.

11. The device of claim 10, further comprising:
    a first electrode of said first pair of fully implantable electrodes positioned proximate a first ventricular chamber to launch a stimulation wave front; and
    a second electrode of said first pair of fully implantable electrodes positioned proximate a second ventricular chamber to sense a local cardiac depolarization between said first electrode and said second electrode,
    wherein the detector detects the cardiac conduction time based on a time between launching the wave front and sensing the local cardiac depolarization.

12. The device of claim 11, wherein the first electrode includes an endocardial electrode positioned within the first ventricular chamber, and the second electrode includes an epicardial electrode positioned on a surface of the second ventricular chamber.

13. The device of claim 11, wherein the first electrode includes an endocardial electrode positioned within the first ventricular chamber, and the second electrode includes an endocardial electrode positioned within the second ventricular chamber.

14. The device of claim 11, wherein the first electrode includes an epicardial electrode positioned on a surface of the first ventricular chamber, and the second electrode includes an epicardial electrode positioned on a surface of the second ventricular chamber.

15. The device of claim 11, wherein the first ventricular chamber is the right ventricular chamber and the second ventricular chamber is the left ventricular chamber.

16. The device of claim 11, wherein the first ventricular chamber is the left ventricular chamber and the second ventricular chamber is the right ventricular chamber.

17. The device of claim 10, wherein the detector senses the conduction time using at least one lead associated with an implantable medical device.

18. The device of claim 10, wherein the detector quantifies a degree of ischemia based on one of an average detected conduction time and the actual detected conduction time for a single conduction time measurement, wherein the average detected conduction time is derived from at least two discrete conduction time measurements.

19. A device comprising:
   means for detecting cardiac conduction time between a first pair of fully implantable electrodes and between a second pair of fully implantable electrodes;
   means for detecting ST segment deviation disposed within a wholly-implantable medical device (IMD);
   means for detecting patient activity level disposed within the IMD; and
   means for indicating myocardial ischemia, also disposed within the IMD, based on the detected conduction time of at least one of said first pair and said second pair of electrodes, wherein the means for indicating myocardial ischemia is based upon each one of: (i) changes in conduction time in combination with ST segment deviation, (ii) changes in conduction time in combination with the detected patient activity level, (iii) the time rate of change of conduction time, and (iv) an average conduction time measurement derived from multiple conduction time measurements wherein conduction time is the detected conduction time between said first pair and said second pair of fully implantable electrodes.

20. The device of claim 19, further comprising:
   a first electrode for launching a stimulation wave front from a first electrode positioned proximate a first ventricular chamber; and
   a second electrode for sensing a local cardiac depolarization at a second electrode positioned proximate a second ventricular chamber,
   wherein the detecting means detects a time between launching the wave front and sensing the local cardiac depolarization.

21. The device of claim 20, wherein the first electrode includes an endocardial electrode positioned within the first ventricular chamber, and the second electrode includes an epicardial electrode positioned on a surface of the second ventricular chamber.

22. The device of claim 20, wherein the first electrode includes an endocardial electrode positioned within the first ventricular chamber, and the second electrode includes an endocardial electrode positioned within the second ventricular chamber.

23. The device of claim 20, wherein the first ventricular chamber is the right ventricular chamber and the second ventricular chamber is the left ventricular chamber.

24. The device of claim 20, wherein the first ventricular chamber is the left ventricular chamber and the second ventricular chamber is the right ventricular chamber.

25. An apparatus, comprising:
   means for detecting cardiac conduction time between at least a first pair and a second pair of fully implantable electrodes coupled to an active wholly-implantable medical device (IMD);
   means for detecting ST segment deviation disposed within the IMD;
   means for detecting patient activity level disposed within the IMD; and
   means for indicating myocardial ischemia, also disposed within the IMD, based on each one of: (i) changes in conduction time in combination with ST segment deviation, (ii) changes in conduction time in combination with the detected patient activity level, and (iii) the time rate of change of conduction time, and wherein conduction time is the detected conduction time between said first pair and said second pair of fully implantable electrodes.

26. An apparatus according to claim 25, further comprising:
   means for launching a stimulation wave front from a first electrode adapted to be positioned proximate a first ventricular chamber; and
   means for sensing a local cardiac depolarization at a second electrode adapted to be positioned proximate a second ventricular chamber,
   and wherein the means for detecting cardiac conduction time includes means for detecting a time between launching the wave front and sensing the local cardiac depolarization.

27. An apparatus according to claim 26, wherein the first electrode comprises an endocardial electrode adapted to be positioned within the first ventricular chamber, and the second electrode comprises an epicardial electrode adapted to be positioned on a surface of the second ventricular chamber.

28. An apparatus according to claim 26, wherein the first electrode comprises an endocardial electrode adapted to be positioned within the first ventricular chamber, and the second electrode comprises an endocardial electrode adapted to be positioned within the second ventricular chamber.

29. An apparatus according to claim 26, wherein the first electrode comprises an epicardial electrode adapted to be positioned on a surface of the first ventricular chamber, and the second electrode comprises an epicardial electrode adapted to be positioned on a surface of the second ventricular chamber.

30. An apparatus according to claim 26, wherein the first ventricular chamber comprises a right ventricular chamber and the second ventricular chamber comprises a left ventricular chamber.

31. An apparatus, according to claim 26, wherein the first ventricular chamber comprises a left ventricular chamber and the second ventricular chamber comprises a right ventricular chamber.

32. An apparatus according to claim 25, further comprising:
   means for detecting the conduction time using at least one lead associated with an implantable medical device.

33. An apparatus according to claim 25, further comprising:
   means for quantifying a degree of ischemia based on the detected conduction time.

* * * * *